(12) United States Patent
Trent et al.

(10) Patent No.: US 8,409,845 B2
(45) Date of Patent: Apr. 2, 2013

(54) ALGAE BIOREACTOR USING SUBMERGED ENCLOSURES WITH SEMI-PERMEABLE MEMBRANES

(75) Inventors: Jonathan D Trent, La Selva Beach, CA (US); Sherwin J Gormly, Carson City, NV (US); Tsegereda N Embaye, Boulder Creek, CA (US); Lance D Delzeit, Santa Clara, CA (US); Michael T Flynn, Corte Madera, CA (US); Travis A Liggett, Redkey, IN (US); Patrick W Buckwalter, La Selva Beach, CA (US); Robert Baertsch, Menlo Park, CA (US)

(73) Assignee: The United States of America as Represented by the Administrator of the National Aeronautics & Space Administration (NASA), Washington, DC (US)

( * ) Notice: Subject to any disclaimer, the term of this patent is extended or adjusted under 35 U.S.C. 154(b) by 1044 days.

(21) Appl. No.: 12/316,557

(22) Filed: Dec. 5, 2008

(65) Prior Publication Data
US 2010/0216203 A1    Aug. 26, 2010

(51) Int. Cl.
   *C12N 1/12* (2006.01)
   *C12M 3/06* (2006.01)
   *A01G 13/00* (2006.01)
(52) U.S. Cl. ............... 435/257.1; 435/292.1; 435/297.1; 47/1.4
(58) Field of Classification Search ............... 435/257.1, 435/292.1; 47/1.4
See application file for complete search history.

(56) References Cited

U.S. PATENT DOCUMENTS

| | | | |
|---|---|---|---|
| 3,955,317 A * | 5/1976 | Gudin | 435/420 |
| 4,043,903 A * | 8/1977 | Dor | 47/1.4 |
| 4,868,123 A | 9/1989 | Berson et al. | |
| 4,888,912 A | 12/1989 | Murray | |
| 6,509,188 B1 | 1/2003 | Trosch et al. | |
| 7,980,024 B2 * | 7/2011 | Berzin et al. | 47/1.4 |
| 2006/0148071 A1 * | 7/2006 | Bauer et al. | 435/290.1 |
| 2008/0009055 A1 | 1/2008 | Lewnard | |
| 2008/0153080 A1 | 6/2008 | Woods et al. | |

(Continued)

FOREIGN PATENT DOCUMENTS

| WO | WO 2008134010 A2 | 11/2008 |
|---|---|---|
| WO | WO 2009/152175 A1 | 12/2009 |

OTHER PUBLICATIONS

Carvalho, et al., Microalgal Reactors: A Review of Enclosed System Designs and Performances, Biotechnol. Prog., Nov. 15, 2006, 1490-1506, 22, American Chemical Society and American Institute of Chemical Engineers.

(Continued)

*Primary Examiner* — William H Beisner
(74) *Attorney, Agent, or Firm* — John F. Schipper; Robert M. Padilla; Christopher J. Menke

(57) ABSTRACT

Methods for producing hydrocarbons, including oil, by processing algae and/or other micro-organisms in an aquatic environment. Flexible bags (e.g., plastic) with $CO_2/O_2$ exchange membranes, suspended at a controllable depth in a first liquid (e.g., seawater), receive a second liquid (e.g., liquid effluent from a "dead zone") containing seeds for algae growth. The algae are cultivated and harvested in the bags, after most of the second liquid is removed by forward osmosis through liquid exchange membranes. The algae are removed and processed, and the bags are cleaned and reused.

39 Claims, 7 Drawing Sheets

U.S. PATENT DOCUMENTS

| | | |
|---|---|---|
| 2008/0160591 A1 | 7/2008 | Willson et al. |
| 2008/0178739 A1 | 7/2008 | Lewnard et al. |
| 2008/0181999 A1 | 7/2008 | Yang |
| 2009/0011492 A1 | 1/2009 | Berzin |
| 2009/0130706 A1 | 5/2009 | Berzin et al. |
| 2009/0305389 A1 | 12/2009 | Willson et al. |
| 2010/0028976 A1 | 2/2010 | Hu et al. |

OTHER PUBLICATIONS

Cheng, et al., Carbon Dioxide Removal From Air by Microalgae Cultured in a Membrane-Photobiorector, Separation Purification Technology, 2006, 324-329, 50, Elsevier B. V.

Fan, et al., Optimization of Carbon Dioxide Fixation by *Chlorella vulgaris*, Cultivated in a Membrane-Photobiorector, Chem. Eng. Technol., 2007, 1094-1099, 30-8, Wiley-VCH Verlag GmbH & Co. KGaA, Weinheim.

Lee, et al., Supplying $CO_2$ to Photosynthetic Algal Cultures by Diffusion through Gas-Permeable Membranes, Applied Microbiology Biotechnology, 1989, 298-301, 31, Springer-Verlag.

Lee, Microalgal Mass Culture Systems and Methods: Their Limitation and Potential, Journal of Applied Phycology, 2001, 307-315, 13, Kluwer Academic Publishers, the Netherlands.

Xu, et al., A Simple and Low-Cost Airlift Photobioreactor for Microalgal Mass Culture, Biotechnology Letters, 2002, 1767-1771, 24, Kluwer Acedemic Publishers, the Netherlands.

\* cited by examiner

ALGAE BIOREACTOR USING SUBMERGED ENCLOSURES WITH SEMI-PERMEABLE MEMBRANES

ORIGIN OF THE INVENTION

This invention was made, in part, by one or more employees of the U.S. government. The U.S. government has the right to make, use and/or sell the invention described herein without payment of compensation, including but not limited to payment of royalties.

FIELD OF THE INVENTION

This invention relates to using flexible enclosures with inflatable, semi-permeable regions in aquatic environments to grow algae and/or other micro-organisms that can be used in the production of oil and other products.

BACKGROUND OF THE INVENTION

Various species of algae are known to produce valuable products ranging from food to fertilizer to biofuels. The large-scale commercial production of these algae however, particularly for commodity products like biofuels, has been limited by the unfavorable economics of the current cultivation and harvesting methods. The two dominant cultivation methods are (1) open raceways and (2) closed bioreactors and two of the dominant harvesting methods are (1) centrifugation and (2) tangential-flow filtration. These cultivation approaches have problems with high associated operating costs, high land costs, uncontrolled evaporation, contamination and/or limited flexibility.

What is needed is a relatively low cost, low maintenance approach for cultivation of the algae and separation of the algae and/or other micro-organisms from other substances. Preferably, the approach should have little or no evaporation or contamination problems and should allow flexibility in throughput, algae choice and other parameters that affect the resulting product(s).

SUMMARY OF THE INVENTION

These needs are met by the invention, which provides a system for cultivating microorganisms, such as algae, some of which are products in themselves and others produce useful byproducts, including oil, food additives, fertilizers, nutriceuticals, and pharmaceuticals. This new cultivating system is an enclosure consisting of plastic or similar bags with patches of inflatable, semi-permeable membranes incorporated into their surfaces. These bags are used in aquatic environments where the water provides infrastructural support through flotation and temperature regulation, the water motion provides mixing within the bag from currents and wave action, and in some locations (e.g., "dead zones") the water chemistry in the surrounding water provides the required nutrients for growing algae or other microorganisms. In addition, by cultivating freshwater organisms in bags deployed in a marine or brackish environment, the surrounding salt water provides a means of dewatering the contents of the bag using patches of membranes that permit forward osmosis (FO).

The bags can be made of a variety of plastics or other impermeable materials and may vary in size and shape. For cultivating algae, the bags will have a transparent upper surface to allow light penetration and may have a reflective lower surface to increase light availability in the bags, provided this does not adversely impact the native populations of algae and/or other micro-organisms in the surrounding environment. The diameter of the individual bag can range from meters to kilometers, but for algae and/or other micro-organisms, the bag thickness is limited to a value, usually no more than about 10 cm, that allows adequate light penetration through water. The bags are made of light-weight, flexible, durable plastic (e.g., polyurethane) or similar material that will be shaped by its flotation on the surface of the water and in some cases by structural components. The shape and flexibility of bags allows the external water currents and waves to mix the bag contents, and the shape and thermal properties of the bag material allows the temperature inside the bag to be regulated by the heat capacity of the surrounding water.

While the size and shape of the bag (other than its depth for growth of algae and/or other micro-organisms) are not critical to the bioreactor's function, the semi-permeable membranes and the offshore location of the bioreactor are critical. The bags have patches of different kinds of semi-permeable membranes on their surfaces, which include gas-permeable, water-permeable, and/or nutrient-permeable membranes. The different membranes function by influencing the dissolved gases, the nutrients, and the concentration of nutrients, salts, and algae and/or other micro-organisms in the bags. Not all the different kinds of membranes are needed, depending on the conditions.

Under most conditions, patches of gas-permeable membranes on the upper surface of the bag, which may be exposed to air, are needed. These membranes allow oxygen and other gasses to pass out of the bag and carbon dioxide to pass into the bag. In some embodiments, pressurized carbon dioxide, available externally or stored in a bladder within the bag, in addition to atmospheric carbon dioxide, will pass through the gas-permeable membranes into the bag.

The liquid-permeable membrane (forward osmosis [FO] membrane) is used to remove liquid from the bag, thereby concentrating the remaining contents of the bag. Liquid, but not algae or other selected micro-organisms, diffuses through the FO membrane into the surrounding liquid, provided there is a chemical gradient between the liquid inside the bag and the liquid outside the bag. Methods of establishing this gradient include: (i) provision of freshwater inside the bag and marine water outside, (ii) provision of marine water inside and brine outside, amd (iii) provision of another substantial concentration differential between the liquids inside and outside the bag. As liquid leaves the bag, chemicals and algae and/or other micro-organisms inside the bag are concentrated within the bag. The concentrated chemicals in the bag may be used to artificially stress the algae and/or other micro-organisms to encourage their production of oil or to induce them to produce other products. Artificial stressors include presence of excess salt and nutrient starvation. The removal of liquid from the bag also concentrates the algae and/or other micro-organisms, which facilitates their harvesting and processing. Under most conditions, after harvesting the bag can be used again.

In one embodiment, the patches of FO membrane are located on the upper surface of the bag so the patches are mostly exposed to air or another ambient atmosphere and do not significantly remove liquid from the bag. In this configuration, osmosis-based liquid removal is initiated by submerging the bags. In another embodiment, the FO membrane is located on the lower surface of the bag, and osmosis proceeds slowly during the entire culturing period. For convenient reference herein, the liquids inside and outside the bag will be collectively referred to as "water."

The nutrient-permeable membranes can be used under conditions in which the nutrients in the surrounding water are higher than in the bag, but are not needed when the bag is filled with high-nutrient water and the nutrient concentration in the surrounding water is low. In environments with high concentrations of nutrients (e.g., "dead zones"), patches of nutrient-permeable membrane are incorporated into the lower surface of the bag to take up nutrients from the surrounding water. Nutrient-permeable membranes, such as nitrate membranes, create an equilibrium between the inside and outside of the bag, but the uptake of nutrients by the algae and/or other micro-organisms (innoculum) inside the bag creates a net flux of nutrients into the bag.

In some embodiments, the bags are filled with nutrient-rich freshwater (non-marine/low salt), for example, from a river mouth or a sewage outfall. The bag is allowed to fill at one end with liquid effluent and either the native population of algae is allowed to grow or the bag is inoculated with an alga or consortium of algae and/or other micro-organisms. Specific strains of algae and/or other micro-organisms can be encouraged to grow by the size of the innoculum and/or by influencing the conditions inside the bag (e.g., light levels, nutrients, pH, salinity, temperature, trace elements).

These culturing and dewatering methods address many of the technical challenges of the existing cultivation and harvesting methods for algae and/or other micro-organisms that impact their cost-effective implementation. A key feature of the new system is that it consists of flexible bags or enclosures that are deployed in aquatic environments. Because the new system is made of light-weight material, such as plastic, and is deployed offshore, this system not only avoids the problems of land costs and competition with other land uses, but the surrounding water provides infrastructure, cooling water, mixing from wave action, and local nutrient supplies. The design of the system avoids problems associated with water use, evaporation, and contamination by "weed" species. When deployed in the contaminated or eutrophied coastal areas known as "dead zones," the system will help to remediate these zones by removing contaminating nutrients. The system will also remove carbon dioxide from the atmosphere and may help to mitigate the contribution carbon dioxide is making to global warming. The energy-intensive de-watering step for conventional algae: harvesting is achieved by the new system, using forward osmosis membranes and requiring little or no external input of energy.

This invention solves many of the current problems associated with cultivating algae in open pond raceways or closed bioreactors on land. These problems include competing land-uses and environmental impact, water requirements, evaporation control, contamination control, temperature regulation, provision of energy for mixing and harvesting, and invasion by "weed" species. The invention also contributes to the remediation of dead zones by removing polluting nutrients and reduces global warming by sequestering carbon dioxide from the atmosphere.

This new system can also be used for cultivating aquatic organisms, including algae and/or other micro-organisms, provided there is a chemical gradient between the growth conditions inside the enclosure and the surrounding environment. The system can also be used for dewatering.

DESCRIPTION OF THE INVENTION

The invention uses an enclosure, such as a plastic bag, as a bioreactor with patches of semi-permeable membranes used for exchanges between the inside and the outside of the bioreactor, in an aquatic environment. For cultivation of algae and/or other micro-organisms, the bag allows light to enter through the upper surface and may have a light-reflective surface on the lower surface to increase the light available for algae cultivation. The bag is filled with a nutrient-rich liquid effluent, which promotes the growth of extant or introduced algae and/or other micro-organisms. The bioreactor is used offshore in an aquatic or marine environment, which provides support, cooling, mixing, dewatering, and in some cases nutrients. The bag-bioreactor is not intended to be used on land, although it can be used in artificial aquatic environments, such as a brine pond, a waste-water basin or a reservoir.

Figure 1:
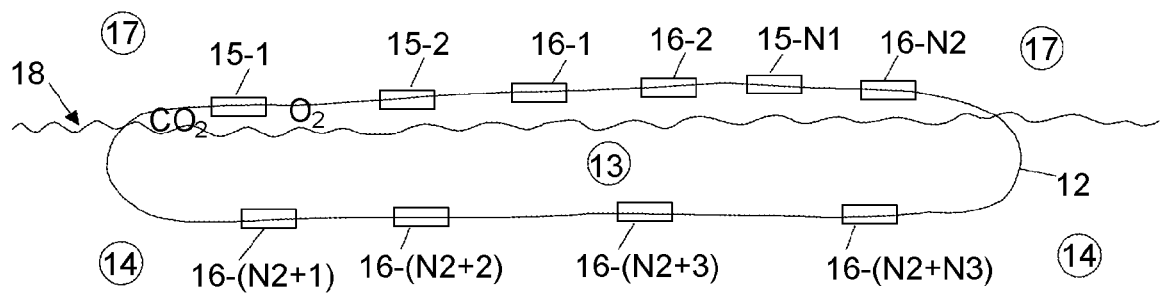
FIG. 1 is a sectional side view of an embodiment of the invention.

The patches of semi-permeable membranes on the bag allow the bag contents to beneficially interact with the surroundings. For example, a gas exchange membrane removes excess $O_2$ from the bag interior and allows $CO_2$ to enter, which aids algae growth. FIG. 1 is a sectional side view of an embodiment 11 of the system. A bag 12, containing a liquid effluent (second liquid) 13 and one or more selected algae and/or other micro-organism(s), is partly submerged in a first liquid 14 of a type different from the second liquid. An upper surface of the bag includes a first sequence 15-$n1$ ($n1$=1, 2, ..., N1; N1≧1) of permeable membrane patches that permit exchange of $CO_2$ outside the bag 12 with $O_2$ inside the bag. The upper surface of the bag 12 optionally includes a second sequence, 16-$n2$ ($n2$=1, ..., N2; N2≧0) of liquid-permeable membrane patches that permit transport of the second liquid 13 from within the bag 12 into the first liquid 14 by forward osmosis (FO). A lower surface of the bag 12 also includes further members, 16-(N2+1), 16-(N2+2), ..., 16-(N2+N3) (N3≧1), of the second sequence of membrane patches that permit transport of the second liquid 13 from within the bag 12 into the first liquid 14. The upper surface of the bag 12 is preferably surrounded by a gas atmosphere 17, such as air, at an ambient pressure, such as 1 atm. The bag is defined by upper and lower bag surfaces, attached to each other to form a closable container, where the upper and lower surfaces are substantially parallel to the surface of the first liquid 14.

Figure 2:
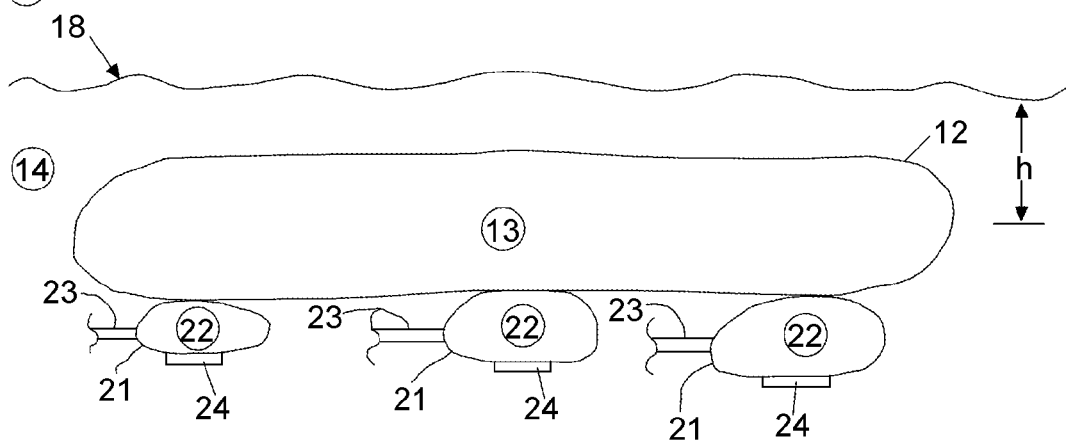
FIGS. 2 and 3A/3B/3C illustrate submersion of the bag in FIG. 1 to a continuously controllable depth using two approaches.

The patches of FO membrane 16-$n2$ remove water to concentrate nutrients, to promote growth of algae and/or other micro-organisms, to concentrate salts or added reagents that induce algal oil production, and to concentrate-algae and/or other micro-organisms to assist in their harvesting and processing. By placing the patches of FO membrane 16-$n2$ on the upper surface of the bag, dewatering can be regulated by controlling the average depth h of the bag below the surface (FIG. 2). When the FO membrane 16-$n2$ is at the surface and mostly exposed to air, little dewatering occurs. When the FO membranes are submerged, the membranes actively dewater the interior of the bag 12. In this first embodiment, the bag 12 is submerged by an average depth h below the surface 18 of the water 14, as illustrated in FIG. 2, to activate the FO process and/or to protect the bag from inclement weather, such as a storm at sea.

In an incubation position, the upper surface of the bag 12 floats adjacent to the water surface 18; and in a second (inverted) position the upper surface and the lower surface positions are exchanged with each other so that the upper surface of the bag is submerged to a selected average depth h (e.g., h=2-20 cm), and all surfaces of the bag are exposed to the surrounding liquid 14 in this second position. Gas exchange ceases and FO (now activated) depletes the bag interior of most of its water 13 and concentrates the algae and/or other micro-organisms grown in the bag interior. In the first approach, the bag 12 is submerged by a ballast arrangement or a tethering arrangement, illustrated in FIGS. 2 and 3A/3B.

The rate of dewatering depends on the properties of the membrane 16-$n2$ and the difference in composition between the water inside and outside the bag as indicated by $$J(\text{eff}) = A\{\Delta\pi - \Delta p\}, \qquad (1)$$

where A is the hydraulic permeability of the membrane by liquid effluent, $\Delta\pi$ is a difference in osmotic pressures (inside versus outside), and $\Delta p$ is a difference in hydrostatic pressure (inside versus outside).

Where hydrostatic pressures are approximately the same, inside and outside the bag 12, $\Delta\pi$ is approximately 400 pounds/in$^2$ across the membrane 16-$n2$ so that the liquid portion of the effluent, not including salts, microorganisms and/or other particles, will diffuse into the surrounding marine water. Where the bag 12 has a depth, measured perpendicular to the water's surface, of no more than about 20 cm, the associated hydraulic pressure difference (water pressure outside the bag minus water pressure inside the bag) is less than 40 pounds/in$^2$ so that the osmotic pressure term M dominates until the bag interior is nearly drained of its liquid effluent. When the bag 12 is nearly fully drained, the bag interior will contain the algae and/or other micro-organisms and other chemicals produced therein, plus a small amount of liquid effluent 13. Before the flux J(eff) changes sign, indicating that some water 14 may flow into the bag 12, it is preferable to terminate the liquid transport, for example, by returning the bag to the surface.

The micro-organisms in the bags will grow over a time interval of 1-10 days or longer. During or at the end of this incubation period, oil-producing algae may be subjected to stresses, such as nitrogen starvation or increased salts to promote oil production in association with algal growth. Some algal species have been found to produce over 40 percent oil, as a fraction of micro-organism dry weight.

When cultures are ready for dewatering, the bag is submerged so that the area primarily exposed to the ambient atmosphere during cultivation is under water. This activates the FO process, which will proceed until the contents of the bag are sufficiently concentrated to facilitate their transport for further processing. Where algae and/or other micro-organisms are present in the bag interior, when the FO has removed sufficient amounts of water to make a thick slurry within the bag interior, the algae and/or other micro-organisms will be pumped out of the bags into a transporting container such as a barge. In the transporting container, the dewatering process can continue to further concentrate the algae and/or other micro-organisms, using FO into sea water or brine (concentrated seawater produced by solar evaporation). After the algae and/or other micro-organisms have been removed from the bag, the bag is available for refilling with nutrient-rich freshwater to re-initiate the growth cycle. The algae and/or other micro-organisms left in the bag after harvesting become the innoculum for the next growth cycle.

To improve the period of use of the bags and clean the semi-permeable membranes, the bag interiors can be periodically rinsed with water. The freshwater algae that will be released into the aquatic environment by this process will not be able to live in seawater or brine.

Another feature of submerging the bags is the enhanced ability of the system to withstand foul weather or harsh sea conditions. For example, when a storm is present or developing locally, submerging the bag 12 to a depth greater than about one half of the wavelength (crest-to-crest distance) of waves, or to depths >20 meters, should allow the bags to withstand severe wind and wave conditions on the surface.

Depth control for a bag is provided, in one embodiment by a fluid-based ballast system that allows the bag to be submerged in a liquid, assumed to be homogeneous, to any reasonable average depth h. One begins with a ballast bag 21, illustrated in FIG. 2, filled with a fluid having an interior pressure p0 and a corresponding volume V0 at atmospheric pressure p(atm). The ballast bag 21 is partly or wholly filled with a fluid 22 at initial pressure p0, using a ballast control mechanism 23, and Boyle's law $$pV = \text{constant} \qquad (2)$$

applies to the bag contents, in the absence of temperature variations. Modest size masses 24 are attached at K spaced apart locations (K≧2) to an underside of the bag exterior or ballast bag exterior, where the individual mass sizes are chosen so that, with the ballast bag interior pressure at p=p0, the bag 12 floats on the surface of the (first) liquid 14. With the bag 12 submerged to an average depth h (≧0) below the liquid surface 18, the pressure on the exterior surface of the bag becomes $$p = p(\text{atm}) + p1 \cdot h, \qquad (3)$$

where p1 is a numerical constant that is characteristic of the liquid 22. At an average depth h for the bag, Boyle's law becomes $$pV = (p(\text{atm}) + p1 \cdot h)V = p(\text{atm})V0, \qquad (4)$$

which can be re-expressed as $$h = (p(\text{atm})/p1)\{(V0/V) - 1\}, \qquad (5)$$

which expresses the average depth h of the bag in terms of the volume V of the bag interior. As fluid is withdrawn from the bag interior (V<V0), the bag average depth h increases continuously and controllably as the bag is submerged below the liquid surface. The average depth h of submersion is preferably limited to values such that the difference, $\Delta\pi - \Delta p$ in Eq. (1) is positive.

The appropriate value for initial bag volume V0, where the bag floats on the (first) liquid surface 18, is determined by taking into account the density and mass of one or more weights attached to the bag. The total mass of the composite bag (bag plus interior fluid plus bag weights) is $$m_c = m_{bag} + \rho_{fluid} V + m_{weight}, \qquad (6)$$

where $\rho_{fluid}$ is the fluid density. The mass of the first liquid displaced by the partly inflated bag is $$m_{Liquid} = \rho_{Liquid} V + m_{weight}(\rho_{Liquid}/\rho_{weight}), \qquad (7)$$

Setting $m_c$ and $m_{Liquid}$ equal to each other results in $$V0 = \{m_{bag} + m_{weight}\{1 - (\rho_{Liquid}/\rho_{weight})\}\}/(\rho_{Liquid}/\rho_{fluid}). \qquad (8)$$

The average depth h of bag submersion may also be controllable by providing hollow, inflatable ribs in the bar surface. When the ribs are partly or wholly inflated with a fluid (e.g., air), the ribs (1) will tend to stiffen and to provide some structure for the bag surface and (2) will act as a flotation device to reduce the bag's tendency to submerge in the surrounding first liquid. The density of the fluid in the bag ribs should be substantially less than the density of the surrounding liquid for the bag.

Figure 3B:
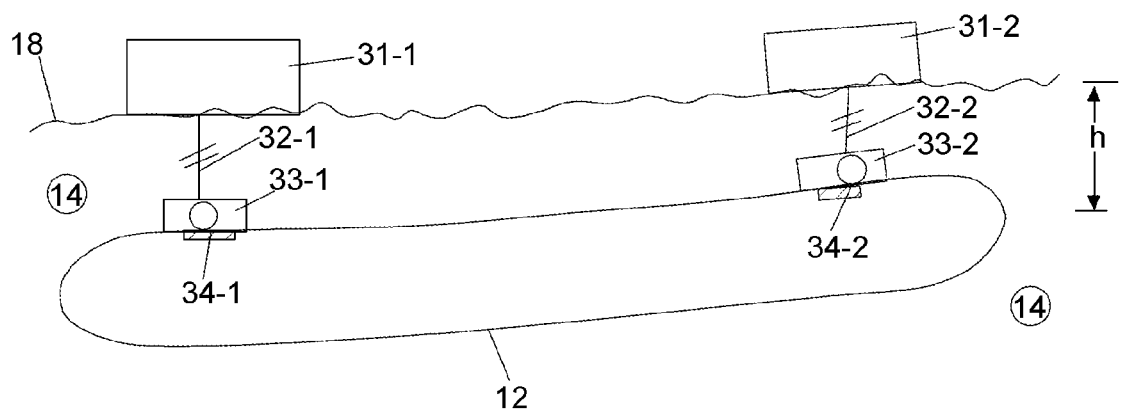
Figure 3A:
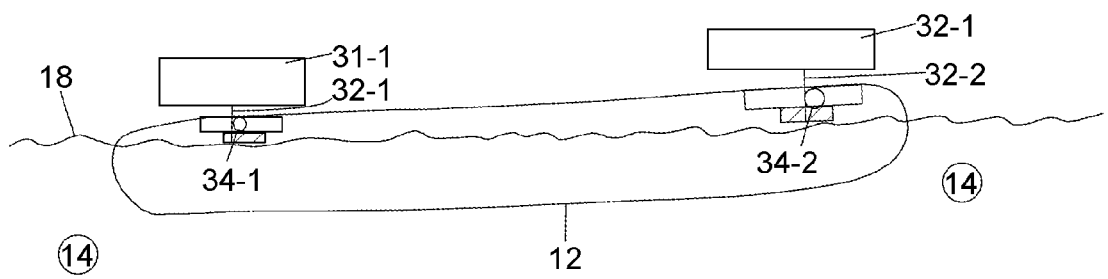
Figure 3C:
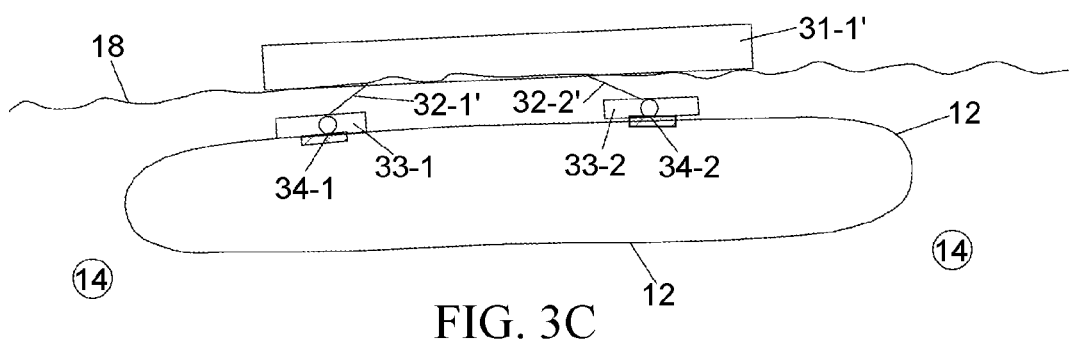

FIGS. 3A and 3B schematically illustrate a second approach for alternatively floating and submerging the bag 12 to a controllable average depth h, relative to a surface 18 of the surrounding water 14. Two or more float modules, 31-1 and 31-2, are connected by respective tethers, 32-1 and 32-2, to floats (optional), and tether roll-up mechanisms, 33-1 and 33-2, respectively, and weights (optional), 34-1 and 34-2, respectively, which are attached at spaced apart locations to the bag 12. In a first position, shown in FIG. 3A, the bag 12 is adjacent to the surface 18 of the water, with the tethers, 32-1 and 32-2, being rolled up or reeled in to the floats, 31-1 and 31-2. In a second position, shown in FIG. 3B, the tethers, 32-1 and 32-2, are rolled out or reeled out a controlled distance d so that the bag 12 is now submerged by an average depth h below the surface 18 of the water 14. FIG. 3C illustrates how two or more tethers, 32-1' and 32-2', can be attached to a single float module 31-1'.

As an alternative to submersion of the bag to a controlled depth, the bag may be "flipped" or inverted so that the bag upper surface (not submerged) and the lower surface (submerged) are interchanged. This maneuver will expose the new lower surface of the bag to the surrounding first liquid; and if this new lower surface has membranes that support FO, the second liquid in the bag interior will be preferentially transported across the membrane(s) in to the surrounding liquid, which will increase the concentration of algae and/or other micro-organisms in the bag interior.

A controlled amount of $CO_2$ is introduced into the bag interior to encourage growth of algae and/or other micro-organisms. If the $CO_2$ forms "bubbles" with average diameters greater than a threshold value, most of the bubbles may rise to an upper surface of the second liquid in the bag and be lost, without contributing to algae growth. One approach for increasing the percentage of $CO_2$ that actually contributes to algae growth is to decrease the average diameter of the $CO_2$ bubbles so that a higher percentage of these bubbles will be absorbed into the second liquid in the bag interior, using a fine mesh screen or a membrane having pores no larger than a selected diameter.

Figure 4A:
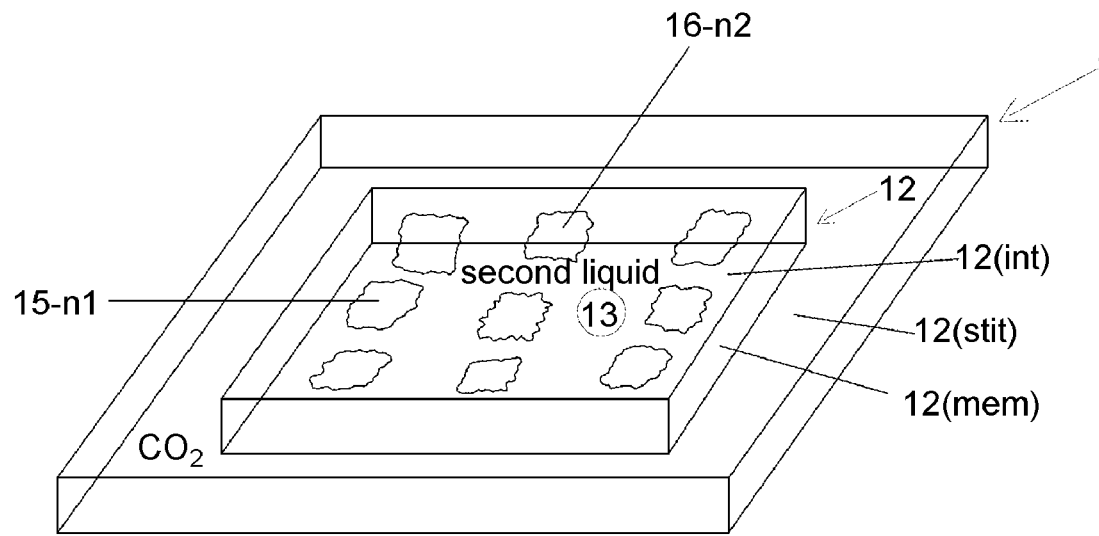
FIGS. 4A/4B illustrate apparatus for controllable $CO_2/O_2$ exchange between the bag interior and an external region.

FIG. 4A illustrates one apparatus for delivering $CO_2$ to the interior 12(int) of the bag. The bag 12 is a rectangular parallelepiped or curvilinear body containing the second liquid 13 and having a sequence of membrane patches, 15-$n1$ and/or 16-$n2$, on an upper surface and/or on a lower surface of the bag. The bag 12 is surrounded by a gas exchange bag 19, and an interstitial space 12(stit) between the bag 12 and the gas exchange bag 19 is filled with $CO_2$ at a selected pressure p($CO_2$), at a partial pressure in a range 1-150 psi. One or more surfaces of the bag 12 contains a membrane 12(mem) that is permeable to $CO_2$ contained in the interstitial space 12(stit), and is, therefore, also permeable to $O_2$ that is produced and accumulates in the bag interior 12(int). Preferably, the $CO_2$ pressure in the interstitial space 12(stit) is greater than the $CO_2$ pressure in the bag interior 12(int) so that the net $CO_2$ flow is into the bag interior. Preferably, the $O_2$ pressure in the bag interior 12(int) is greater than the $O_2$ pressure in the interstitial space 12(stit) so that the net $O_2$ flow is into the interstitial space. The gas exchange bag walls are not permeable to $CO_2$ or to $O_2$. Proceeding in this manner, a net transfer of $CO_2$ into bag interior occurs and a net transfer of $O_2$ into the interstitial space occurs. The $O_2$ in the interstitial space 12(stit) can be partly or wholly removed by methods known in the art so that an appreciable amount of $O_2$ does not accumulate in the interstitial space.

Figure 4B:
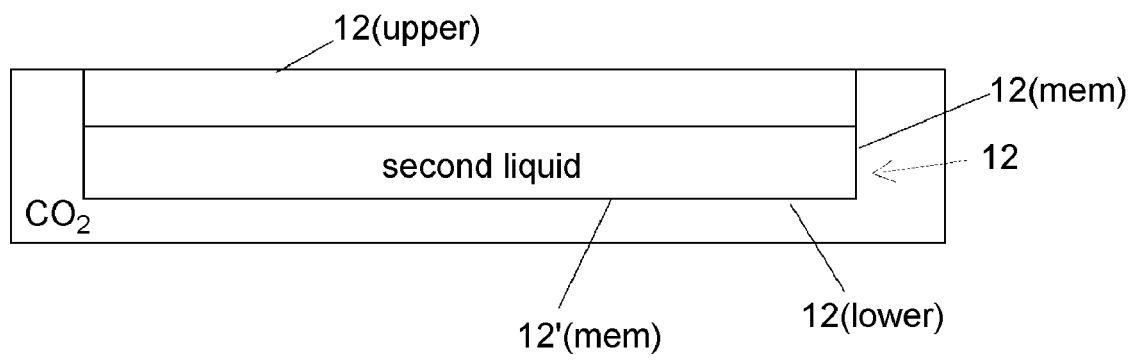

An alternative apparatus, shown in side view in FIG. 4B, provides a lower region 19(lower) and/or an upper region 19(upper) that also contains $CO_2$ at the selected pressure p($CO_2$). The lower region 19(lower) and/or the upper region 19(upper) is optionally separated from the bag interior 12(int) by a membrane 12(mem) that is permeable to $CO_2$ (and to $O_2$).

Figure 5A:
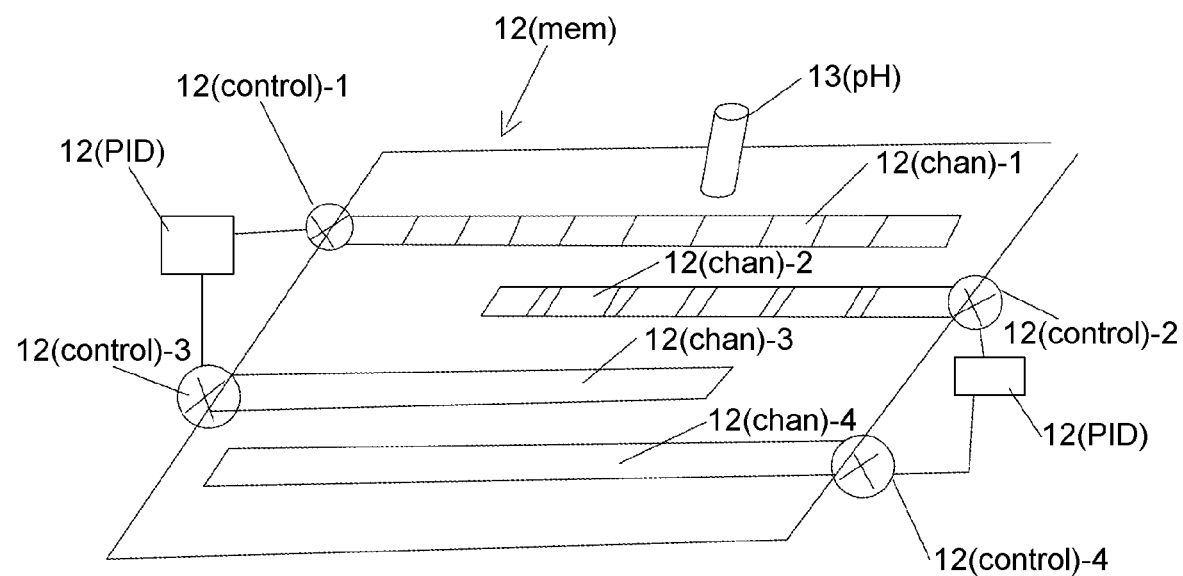
FIGS. 5A/5B/5C illustrate alternative channel arrangements for membranes for $CO_2/O_2$ exchange.
Figure 5B:
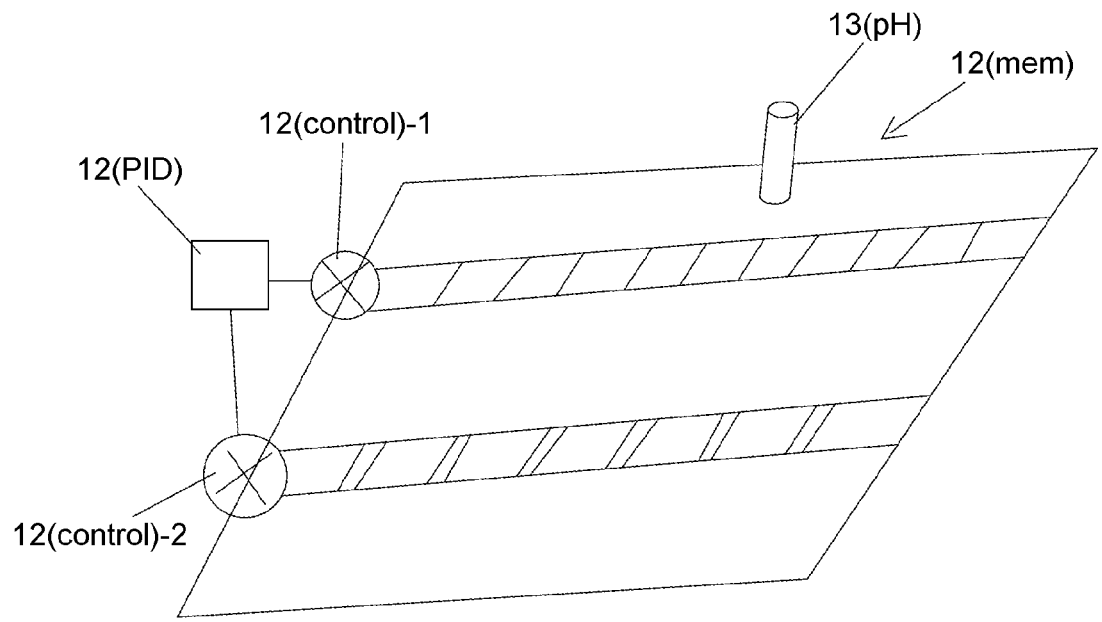

FIGS. 5A/5B/5C illustrate a suitable arrangement of gas-permeable membranes 12(mem) that can be provided on an upper surface, a bottom surface and/or a side surface of the bag 12, to facilitate exchange of $CO_2$ and of $O_2$ between regions outside the bag and inside the bag. In FIG. 5A, the membranes 12(mem) extend as M linear or curvilinear channels or fingers 12(chan)-m (m=1, ..., M; M≧1) from a first surface toward a second surface of the bag 12. In FIG. 5B, the membranes 12(mem) extend as channels or fingers (12(chan)-m from a first surface to a second surface of the bag 12. One or more of the channels contains a $CO_2$ control valve mechanism 12(control)-m that either shuts off flow of $CO_2$ into the associated finger or permits flow of $CO_2$ at a selected pressure p($CO_2$) into the associated channel. The control mechanisms 12(control)-m are individually controlled by one or more PID controllers 12(PID) that determine which valves 12(control)-m are open and which valves are closed.

Figure 5C:
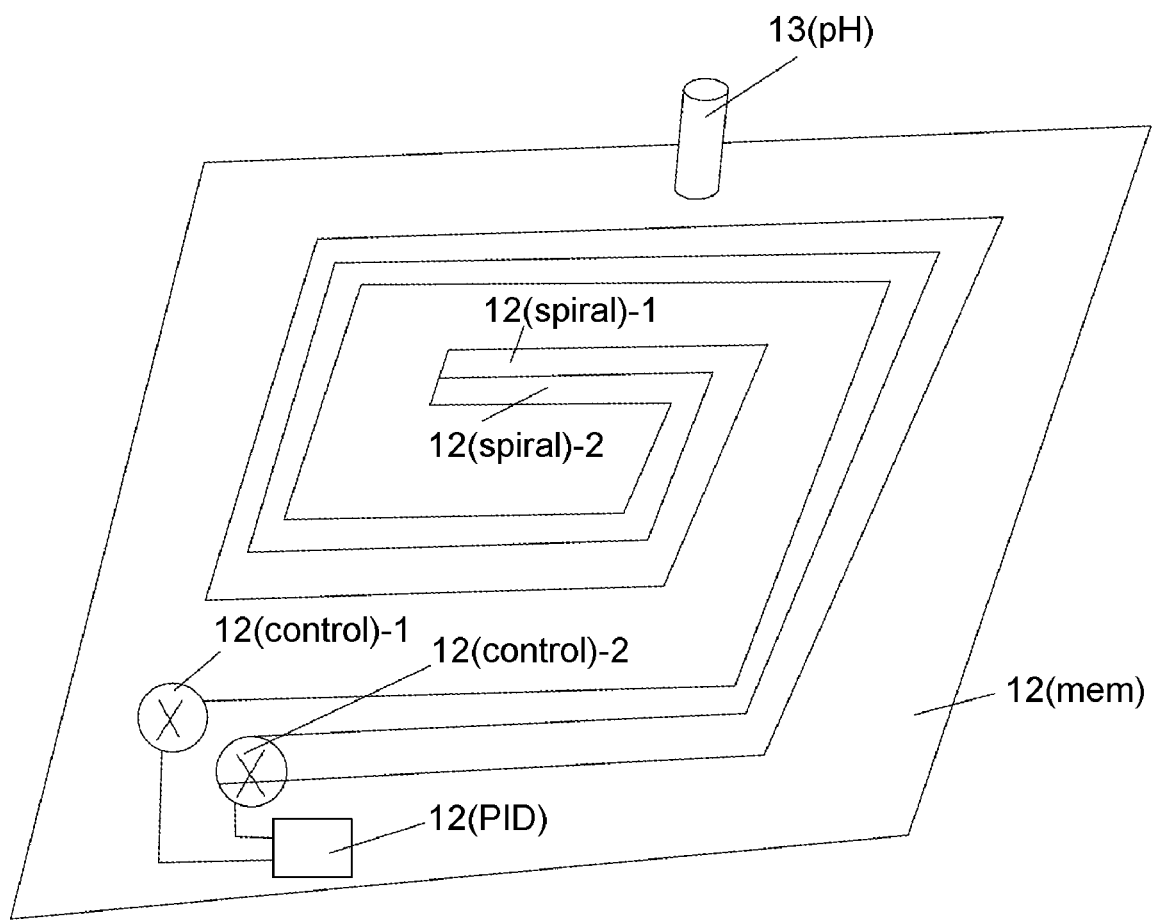

FIG. 5C illustrates a spiral arrangement of channels in which each of M adjacent spiral channels 12(spiral)-m (m=1, ..., M; M≧1; here, M=2) has a membrane along one surface that interfaces with the bag interior, to permit $CO_2$ exchange with the bag interior. In each of the embodiments in FIGS. 5A, 5B and 5C, a pH meter 13(pH) is preferably provided to monitor the pH in the bag interior (not shown here) for purposes of growth of the algae and/or other μorgs.

The algae may include one or more of *botryococcus braunii, chlorella vulgaris* or another lipid-producing algae that is useful for producing hydrocarbons or other desired products. *Botryococcus braunii* (Bb) is a pyramid-shaped, freshwater green algae, with colonies held together by a lipid biofilm matrix. The species is best known for its ability to produce large amounts of hydrocarbons, especially oils in the form of triterpenes, which are typically 30-40 percent of the dry weight of the triterpenes. Bb is believed to grow best at a temperature T≈23° C., with a light intensity of 60 Watts/cm², with a light period of about 12 hours per day, at a salinity level of 0.15 M NaCl. The oils produced are usually unbranched isoprenoid triterpenes having a chemical composition $C_nH_{2n-10}$, (n=23-37), with n=30-37 accounting for as much as about 70 percent of the total triterpenes. The oils produced through hydro-cracking include octane (gasoline), kerosene, diesel, aviation fuel, residual oil, alkanes, alkenes, alkynes, alcohols, ethers, aldehydes, ketones, esters, amines, amides, benzene ring-based hydrocarbons and cyclic hydrocarbons.

Bb performs moderately well as a lipid-based feedstock for fuel production, with a doubling time for growth of 48-72 hours, depending on the growth environment. Some experimental results indicate that, where supplemental $CO_2$ (1-2 percent) is provided, the concentrations of palmitic acid and oleic acid produced are increased by factors of 2-3, relative to the corresponding concentrations produced in air; hydrocarbon content was found to be above 20 percent where 2 percent supplemental $CO_2$ was provided. Other experimental results indicate that growth of Bb in water with salinity levels of 0.034 M and 0.085 M NaCl, produces approximately twofold increases in concentrations of palmitic acid and oleic acid in the Bb grown.

*Chlorella vulgaris* (Cv) is a spherical-shaped, single-celled green algae and contains green photosynthetic pigments, chlorophyll-a and chlorophyll-b, with associated photosynthetic efficiency as high as about 8 percent. When dried, the plant is about 45 percent protein, 20 percent fat, 20 percent carbohydrate, 5 percent fiber and 10 percent minerals and vitamins. The genus, *chlorella* can grow in direct sunlight, with a solar energy conversion efficiency of about 20 percent, in the presence of high levels of nitrates and phosphates. Cv is more often associated historically with food and food additive feedstocks than with feedstocks for oil production. However, Cv can also serve as a feedstock for algal oil, for trans-esterification into bio-diesel. Cell wall rupture is an essential step in extracting lipids and reusing the cell walls for fermentation into ethanol, subsequently used in the trans-esterification process. Bio-diesel and ethanol, produced from trans-esterification of Cv, provide 3.20 and 1.34 energy-equivalent units, relative to the 1.0 energy-equivalent unit solar energy input. The estimated energy gain for bio-diesel produced from Cv is about 4:1. One concern is the choice of enzymes to optimize production (increase the production rate) of bio-diesel fuel. Another concern is removal of products of the process that are not algal oil.

Thus far, the discussion of this invention has focused on growth of algae and/or other micro-organisms within the bag interior, for provision of oil for diesel, aircraft and automotive vehicles and for provision of other useful products for nutritional needs and other chemical applications. This invention can also used to encourage growth of other macro-organisms within the bag interior, such as shrimp, prawns, crayfish and/or crabs.

Figure 6:
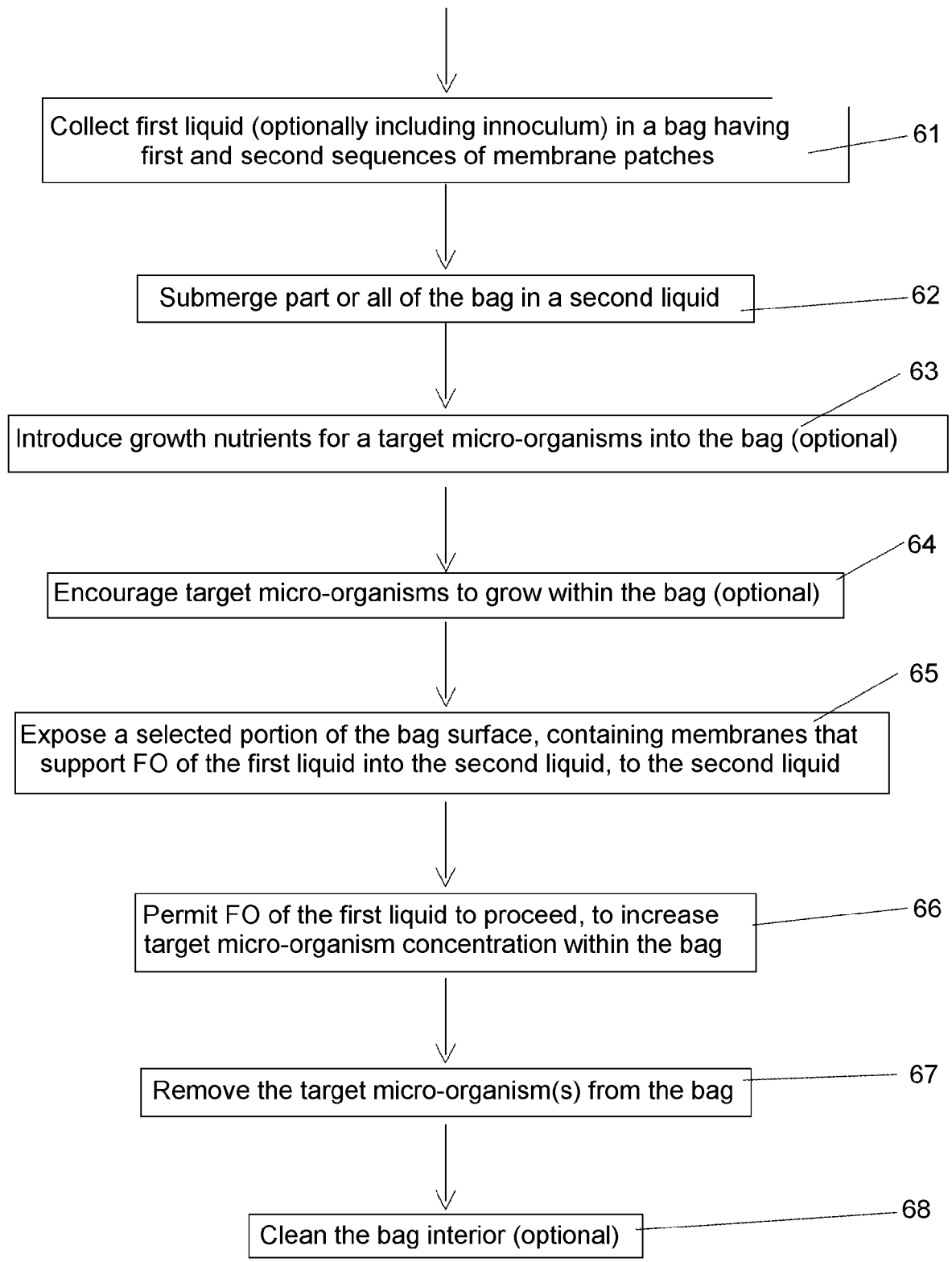
FIG. 6 is a flow chart of a procedure for practicing the invention.

FIG. 6 is a flow chart illustrating a method for practicing the invention. In step 61, effluent or eutrophied second liquid is collected in a bag. The liquid effluent may include a modest concentration of target micro-organisms, such as algae, bacteria, etc., that provide an innoculum or "seed" for one or more desired species to be grown within the bag. In step 62, a selected surface, or all of the surface, of the bag is submerged in a first liquid, which has a differential concentration of at least one chemical substance relative to the second liquid.

In step 63 (optional), $CO_2$, $NH_3$ and/or other growth nutrients for a target micro-organism are introduced into the bag interior. In step 64 (optional), the target micro-organisms are permitted, or encouraged, to grow within the bag. In step 65, a selected portion of the bag surface, containing membranes that support FO of the second liquid into the first liquid, is exposed to the first liquid. In step 66, FO of the second liquid into the first liquid, across the FO membranes, is permitted to proceed so that at least a portion of the second liquid is removed from the bag interior, thereby increasing a relative concentration of the target micro-organism within the bag contents. In step 67, the target micro-organism(s), now at increased concentration, and remainder of the second liquid are removed from the bag interior. In step 68 (optional), the bag interior is cleaned and made ready for a new cycle.

The contents of the bag interior may include lipid-based substances that can be further processed to provide oil for diesel, aircraft, automotive vehicles and other uses, using processes that are well known in the art. Alternatively or additionally, non-marine water (originally the second liquid) that is transported through the second sequence of FO membrane patches 16-*n*2 (FIG. 1) can be used to locally modify or remediate the high-nutrient-load water (first liquid) that surrounds the bag. Where a sufficient number of bags is provided in a given "dead zone," this dead zone can be partly or fully converted to a reduced-nutrient zone that again supports aquatic life.

Figure 7:
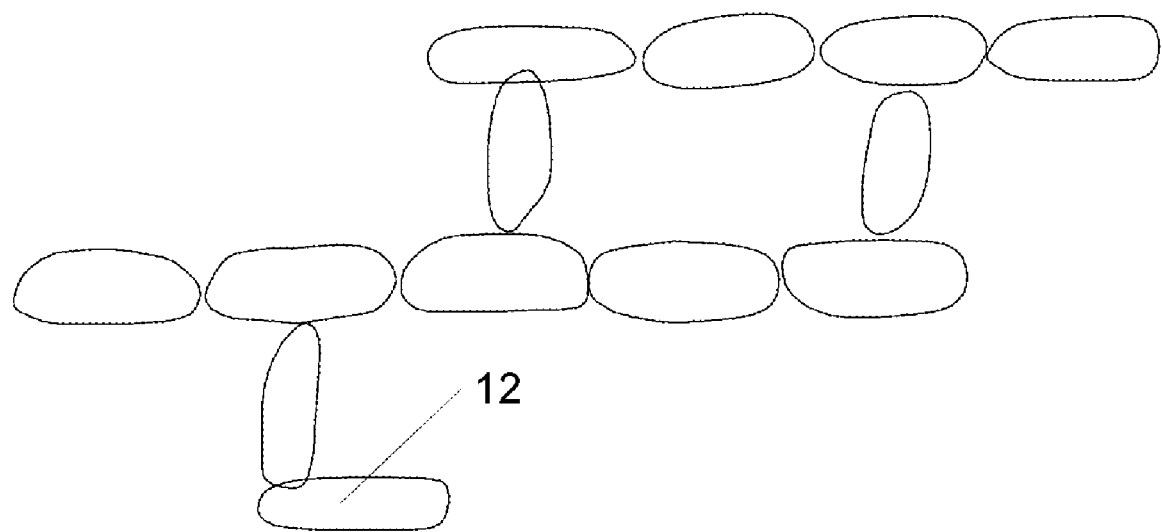
FIG. 7 schematically illustrates a connected structure for bag transport.

Two or more bags 12 can be attached to each other to form a "connected structure," illustrated in FIG. 7, for immobilizing the bags or for transport of the bags in the water. In a connected structure, resembling a linear or branched carbon (backbone) chain, each bag is attached to at least one other bag, and a first bag in the structure can be reached from a second bag in the structure by a path that stays within the structure.

What is claimed is:

1. A method for producing at least one micro-organism ("μorg"), the method comprising:
   providing a closeable enclosure, having an enclosure interior and being defined by first and second opposed enclosure surfaces that are joined together;
   partially or fully immersing the enclosure in a first type liquid;
   partially filling the enclosure with the at least one μorg and a second type liquid;
   closing the enclosure with the second type liquid and the at least one μorg contained in the enclosure interior, where at least one of the enclosure first and second surfaces comprises one or more semi-permeable first membranes that are permeable to the second type liquid and are substantially impermeable to the at least one μorg;
   allowing at least a portion of the second type liquid within the enclosure interior to pass through the one or more first membranes into the first type liquid by forward osmosis, to thereby remove at least a portion of the second type liquid in the enclosure interior;
   providing at least one of the enclosure first surface and the enclosure second surface with at least one $CO_2$ transport membrane having a $CO_2$ transport rate across the transport membrane that can be changed; and
   increasing or decreasing the rate of $CO_2$ transport across the transport membrane into said enclosure, in order to bring a present $CO_2$ concentration value, $C(CO_2)$, into closer agreement with a selected $CO_2$ concentration value, $C(CO_2; ref)$.

2. The method of claim 1, further comprising removing said at least one μorg from said enclosure interior when said at least one μorg has reached at least a selected μorg growth stage.

3. The method of claim 1, further comprising:
   providing said at least one or more semi-permeable first membranes on said enclosure first surface; and
   submerging said enclosure first surface in order to promote transport of said second type liquid through said one or more first membranes into said first type liquid.

4. The method of claim 1, further comprising choosing said first type liquid/second type liquid to have a non-zero gradient of a selected chemical across at least one of said one or more first membranes.

5. The method of claim 4, further comprising choosing a combination of said first type liquid/second type liquid to be at least one of marine water/non-marine water, brine/marine water, and brine/non-marine water.

6. The method of claim 4, further comprising choosing said second type liquid to comprise effluent water.

7. The method of claim 1, further comprising initially positioning said enclosure so that a portion of said enclosure second surface is initially submerged in said first type liquid to influence passage of said second type liquid through at least one of said one or more of said first membranes.

8. The method of claim 1, further comprising providing de-eutrophication of a portion of said first type liquid adjacent to said enclosure first surface by passage of said portion of said second type liquid through said one or more first membranes into said first type liquid.

9. The method of claim 1, further comprising increasing salinity of said second type liquid within said enclosure.

10. The method of claim 1, further comprising selecting at least one of said one or more first membranes from a group of semi-permeable membranes that contain small pores and are hydrophobic.

11. The method of claim 1, further comprising choosing said one or more first membranes to have a thickness in a range 1-20 mils.

12. The method of claim 1, further comprising choosing said at least one µorg to be an alga that produces at least one lipid.

13. The method of claim 12, further comprising choosing said at least one lipid-producing alga to include at least one animal feed compound.

14. The method of claim 12, further comprising choosing said at least one lipid-producing alga to include at least one fertilizer component.

15. The method of claim 12, wherein said at least one lipid-producing compound produces a compound drawn from a group of hydrocarbons consisting of fuel oil, diesel fuel, aviation fuel, gasoline, kerosene, alkanes, alkenes, alkynes, alcohols, ethers, aldehydes, ketones, esters, amines, amides, benzene ring-based hydrocarbons and cyclic hydrocarbons.

16. The method of claim 1, further comprising removing a portion of said second type liquid and said at least one µorg from said enclosure interior at first and second selected times that are spaced apart from each other.

17. The method of claim 16, further comprising choosing a difference between said second selected time and said first selected time to be no greater than about ten days.

18. The method of claim 1, further comprising removing, from said enclosure, and processing said at least one µorg, to produce at least one lipid with a lipid weight of at least 20 percent dry weight of said at least one µorg, and to serve as an inocculum for subsequent growth of said µorg.

19. The method of claim 1, further comprising submerging said enclosure in said first type liquid to a continuously variable or discretely variable, selected depth h so that said enclosure is substantially completely submerged below a surface of said first type liquid.

20. The method of claim 19, wherein said process of submerging said enclosure in said body of said first type liquid to said selected depth h comprises:
providing at least two inflatable submersion enclosures, attached to said enclosure to be submerged, with each submersion enclosure having a selected weight attached thereto and being partly filled with a selected fluid that has a lower density than said first type liquid and a lower density than said second type liquid, where the sum of the weights attached to a submersion enclosure is selected so that (i) when all of the selected fluid is withdrawn from all the submersion enclosures, the enclosure to be submerged will sink toward a bottom of said first type liquid and (ii) when sufficient fluid is admitted into the plurality of submersion enclosures, the enclosure to be submerged will float on said surface of said first type liquid,
whereby said depth of said enclosure is continuously or discretely varied by withdrawing the selected fluid from, or adding the selected fluid to, at least one submersion enclosure.

21. The method of claim 19, wherein said process of submerging said enclosure to be submerged in said body of said first type liquid to said selected depth h comprises:
providing one or more float modules that are capable of floating on or near said liquid surface;
providing one or more tethers, each tether having a first end attached to at least one float module and having a second end attached to or associated with said enclosure;
providing a tether roll-up/reel-out mechanism, located adjacent to the first end or adjacent to the second end of each of the one or more tethers, that decreases a length d of the associated tether or increases the length d of the associated tether, upon receipt of a roll-up command signal or a reel-out command signal, respectively; and
providing a roll-up/reel-out command control mechanism, connected to each of the at least two tether roll-up/reel-out mechanisms, to provide a roll-up command signal or, alternatively, a reel-out command signal to the tether roll-up/reel-out mechanism,
whereby said depth h of said enclosure is continuously varied or discretely varied by varying the length d of the associated tether.

22. The method of claim 19, further comprising controllably submerging said enclosure first surface to a depth in a range of 0-20 meters below said first type liquid surface.

23. The method of claim 19, further comprising providing at least one of said enclosure first surface and said enclosure second surface with at least one hollow core rib that can be inflated by introduction of a selected fluid into the at least one hollow core rib.

24. The method of claim 1, further comprising:
providing N enclosures (N≧2), produced according to claim 3; and
attaching each of the N enclosures to at least one of the other N−1 enclosures so that the N enclosures form a connected structure that can be moved in said body of first type liquid from a first location to a second location that is spaced apart from the first location.

25. The method of claim 1, further comprising:
partially or fully immersing said enclosure in said first type liquid; and
allowing heat capacity of said first type liquid to subsequently maintain a temperature of said second type liquid approximately equal to a temperature of said first type liquid.

26. The method of claim 1, further comprising allowing wave action in said first type liquid to thereby promote mixing of contents of said second type liquid within said enclosure.

27. The method of claim 1, further comprising providing said second type liquid within said enclosure with an average depth having a range within said enclosure of 5-20 cm.

28. The method of claim 1, further comprising allowing light that is incident on said enclosure, to illuminate said at least one µorg and to promote growth of said at least one µorg within said enclosure.

29. The method of claim 28, further comprising providing said enclosure second surface with an enclosure interior surface that receives and reflects substantially all light incident thereon within a selected wavelength range.

30. The method of claim 1, further comprising providing said enclosure first surface with an enclosure substance that receives incident light and transmits the incident light into said second type liquid only if at least one wavelength of the incident light is within a selected wavelength range.

31. The method of claim 1, wherein said at least one $CO_2$ transport membrane includes a plurality of mesh screen apertures that provide gas bubbles containing $CO_2$ gas having gas bubble diameters less than a selected threshold diameter, within said enclosure interior, to thereby promote absorption of said $CO_2$ gas bubbles within said second type liquid.

32. The method of claim 1, further comprising:
providing at least one second membrane that permits transport of $O_2$ from said enclosure interior to an exterior of said enclosure.

33. The method of claim 1, further comprising:
providing a controller that controls said present $CO_2$ concentration value $C(CO_2)$ within said second type liquid relative to said selected $CO_2$ concentration value, $C(CO_2; ref)$.

34. A method for producing at least one micro-organism ("μorg"), the method comprising:
providing a first type liquid;
providing a sealable enclosure, having an enclosure interior and being defined by first and second enclosure surfaces;
partially filling the enclosure interior with a second type liquid, and providing at least one selected micro-organism ("μorg") in the enclosure interior;
closing the enclosure;
positioning the enclosure in the first type liquid;
providing at least one of the first and second enclosure surfaces with one or more semi-permeable first membranes that are permeable to at least one of $CO_2$ gas and $NH_3$ gas and are substantially impermeable to the at least one selected μorg;
providing an exterior source of at least one of $CO_2$ gas and $NH_3$ gas in contact with the one or more first membranes;
providing a controller that senses a pH value, pH(sens), within the second type liquid, compares the value pH(sens) with a reference value, pH(ref), for the pH value within the second type liquid, and introduces at least one of the $CO_2$ gas and the $NH_3$ gas into the second type liquid in order to bring pH(sens) into closer agreement with pH(ref);
providing a semi-permeable second membrane, positioned on at least one of the first and second enclosure surfaces, that is permeable to the second liquid and is not permeable to the at least one μorg; and
allowing at least a portion of the second type liquid within the enclosure interior to pass through the second membrane, positioned on at least one of the first and second enclosure surfaces, into the first type liquid by forward osmosis, to thereby remove at least part of the second type liquid from the enclosure interior.

35. The method of claim 34, further comprising choosing said pH reference value in a range $3.5 \leq pH(ref) \leq 9.5$.

36. A method for producing at least one micro-organism ("μorg"), the method comprising:
providing a sealable enclosure, having an enclosure interior and being defined by first and second opposed enclosure surfaces that are joined together;
partially or fully immersing the enclosure in a first type liquid;
partially filling the enclosure with the at least one μorg and a second type liquid;
closing the enclosure with the second type liquid and the at least one μorg contained in the enclosure interior, where at least one of the enclosure first and second surfaces comprises one or more semi-permeable first membranes that are permeable to the second type liquid and are substantially impermeable to the at least one μorg;
allowing at least a portion of the second type liquid within the enclosure interior to pass through the one or more first membranes into the first type liquid by forward osmosis, to thereby remove at least a portion of the second type liquid in the enclosure interior;
providing the one or more first membranes on the enclosure first surface; and
positioning at least one of the one or more first membranes above a surface of the first type liquid in order to reduce or suppress transport of said second liquid through the first membrane into said first type liquid.

37. A method for producing at least one micro-organism ("μorg"), the method comprising:
providing a sealable enclosure, having an enclosure interior and being defined by first and second opposed enclosure surfaces that are joined together;
partially or fully immersing the enclosure in a first type liquid;
partially filling the enclosure with the at least one μorg and a second type liquid;
closing the enclosure with the second type liquid and the at least one μorg contained in the enclosure interior, where at least one of the enclosure first and second surfaces comprises one or more semi-permeable first membranes that are permeable to the second type liquid and are substantially impermeable to the at least one μorg;
allowing at least a portion of the second type liquid within the enclosure interior to pass through the one or more first membranes into the first type liquid by forward osmosis, to thereby remove at least a portion of the second type liquid in the enclosure interior; and
providing one or more second membranes on at least one of the first enclosure surface and the second enclosure surface, which are permeable to at least one selected nutrient for the at least one μorg.

38. A method for producing at least one micro-organism ("μorg"), the method comprising:
providing a sealable enclosure, having an enclosure interior and being defined by first and second opposed enclosure surfaces that are joined together;
partially or fully immersing the enclosure in a first type liquid;
partially filling the enclosure with the at least one μorg and a second type liquid;
closing the enclosure with the second type liquid and the at least one μorg contained in the enclosure interior, where at least one of the enclosure first and second surfaces comprises one or more semi-permeable first membranes that are permeable to the second type liquid and are substantially impermeable to the at least one μorg;
allowing at least a portion of the second type liquid within the enclosure interior to pass through the one or more first membranes into the first type liquid by forward osmosis, to thereby remove at least a portion of the second type liquid in the enclosure interior; and
adding a selected chemical to the second type liquid to promote production of at least one of $CO_2$ and $NH_3$ within the enclosure.

39. A method for producing at least one micro-organism ("μorg"), the method comprising:
providing a sealable enclosure, having an enclosure interior and being defined by first and second opposed enclosure surfaces that are joined together;

partially or fully immersing the enclosure in a first type liquid;

partially filling the enclosure with the at least one μorg and a second type liquid;

closing the enclosure with the second type liquid and the at least one μorg contained in the enclosure interior, where at least one of the enclosure first and second surfaces comprises one or more semi-permeable first membranes that are permeable to the second type liquid and are substantially impermeable to the at least one μorg;

allowing at least a portion of the second type liquid within the enclosure interior to pass through the one or more first membranes into the first type liquid by forward osmosis, to thereby remove at least a portion of the second type liquid in the enclosure interior; and applying a process of inverting positions of said enclosure first surface and said enclosure second surface, relative to a surface of said first liquid, to reduce or terminate forward osmosis that has begun across the one or more first membranes.

* * * * *